United States Patent [19]

Grim et al.

[11] Patent Number: 4,953,543

[45] Date of Patent: Sep. 4, 1990

[54] CRUCIATE LIGAMENT LEG BRACE

[75] Inventors: Tracy E. Grim, Broken Arrow, Okla.; Jeffrey R. Haines, Encino, Calif.

[73] Assignee: Royce Medical Company, Westlake Village, Calif.

[21] Appl. No.: 230,445

[22] Filed: Aug. 9, 1988

[51] Int. Cl.$^5$ ................................................. A61F 5/00
[52] U.S. Cl. .................................... 128/80 C; 128/80 F
[58] Field of Search ................. 128/80 R, 80 B, 80 C, 128/80 F, DIG. 20; 2/22; 623/27

[56] References Cited

U.S. PATENT DOCUMENTS

| | | | |
|---|---|---|---|
| 891,181 | 6/1908 | Mitchell | 128/87 R |
| 2,229,271 | 1/1941 | Anderson | 128/87 R |
| 2,531,486 | 11/1950 | Weber | 128/80 E |
| 3,762,405 | 10/1973 | DeGeorge | 128/88 |
| 4,271,831 | 6/1981 | Deibert | 2/22 |
| 4,481,941 | 11/1984 | Rolfes | 128/80 C |
| 4,614,181 | 9/1986 | Karlsson | 128/80 C |
| 4,697,583 | 10/1987 | Mason et al. | 128/80 C |

*Primary Examiner*—Robert A. Hafer
*Assistant Examiner*—Kevin G. Rooney
*Attorney, Agent, or Firm*—Poms, Smith, Lande & Rose

[57] ABSTRACT

A leg brace for alleviating problems with torn or damaged anterior or posterior cruciate ligaments includes an upper assembly oriented longitudinally with and extending circumferentially around the thigh, a lower assembly oriented longitudinally with and extending circumferentially around the calf, and hinge assemblies connecting the upper and lower assemblies and with axes oriented along the axis of rotation of the knee joint. Two pairs of elongate support struts are provided with one pair extending along the medial and lateral portions of the thigh and the other extending along the medial and lateral portions of the calf and with the central ends of both pairs of struts connected to the hinge assemblies. Straps are provided with the upper and lower assemblies and which extend circumferentially around the thigh and calf respectively for securing the leg brace to the wearer's leg. Padding is provided with the upper and lower assemblies and which extend circumferentially around the thigh and calf respectively. On the lower assembly, separate anterior and posterior cruciate ligament support plate assemblies are provided for applying independently variable posteriorly and anteriorly directed forces against the tibia. Each support plate assembly is independently attached to the lower assembly's pair of elongate support struts and may be independently vertically adjusted through vertical slots in the support struts to accommodate different leg sizes. A support collar may be utilized to grip the wearer's leg just above the ankle and thereby prevent downward slippage or pistoning of the leg brace during use.

27 Claims, 3 Drawing Sheets

CRUCIATE LIGAMENT LEG BRACE

FIELD OF THE INVENTION

This invention relates to a leg brace for injured knees. More particularly it relates to a hinged leg brace adapted for alleviating problems with torn or weakened anterior or posterior cruciate ligaments.

DESCRIPTION OF THE PRIOR ART

A great many approaches have been proposed in the prior art for leg braces of various types. For example, reference may be made to U.S. Pat. Nos. 2,144,641; 3,575,166; 3,669,105; 4,136,404; and 4,489,717 showing a variety of braces for protection and support of knee joints and legs. However, non of these prior art braces have been totally satisfactory in alleviating problems with torn or weakened cruciate ligaments. The cruciate ligaments are a pair of crossed ligaments which connect the femur, the upper leg bone, and the tibia, the main lower leg bone, and which provide the primary means of controlling forward and rearward movement of the tibia relative to the femur, in cooperation with associated musculature and soft tissue complexes. The anterior cruciate ligament controls forward movement or "drawer-like" shifting, while the posterior cruciate ligament controls rearward movement or "drawer-like" shifting, of the tibia relative to the femur.

Applicants have determined that in order for a brace to be effective in providing relief for injuries to either or both anterior and posterior cruciate ligaments, while simultaneously being adaptable for use by wearers with varying degrees of damage to these ligaments as well as varying leg sizes, a brace must include certain features. Thus, such a leg brace must include an adjustable hinge system that allows the brace to either limit movement or "Range of Motion" (R.O.M.), or to bend in a fashion that approximates the natural bending of the knee, and a system for applying independently variable amounts of posteriorly and anteriorly directed force to the tibia while simultaneously allowing for independent vertical adjustment of the application points of these oppositely directed forces. These features allow a leg brace to simulate the type of control over forward and rearward drawer shifting provided by healthy anterior and posterior cruciate ligaments.

Applicants are not aware of any prior art leg braces either directed to the application of such independently vertically adjustable tibia directed forces or in any way capable of achieving such application of forces.

Various prior art knee prostheses have been proposed heretofore. Examples of such prostheses are shown in U.S. Pat. Nos. 4,381,768; 4,372,298; and 4,271,831, in addition to the patents cited hereinabove. However, none of these prior knee prostheses had a structural arrangement capable of applying independently vertically adjustable front and rear tibia directed, and unidirectional forces to accommodate varying leg sizes and knee problems.

Reference is also made to U.S. Pat. No. 4,697,583, which provides a leveraging system that applies an anteriorly directed force to the femur and a posteriorly directed force to the tibia. However, this knee prosthesis is directed exclusively to problems with anterior cruciate ligaments and is not directed to alleviating problems with posterior cruciate ligaments. In addition, this reference has no structural arrangement allowing for independent vertical adjustment of the application points of its anteriorly and posteriorly directed forces.

Further, U.S. Pat. No. 4,407,276, shows a hinged leg brace having adjustments for accommodating varying leg sizes and having a plurality of straps for circumferentially gripping the leg and holding the brace in position. However, this knee prosthesis is directed primarily to controlling the degree of motion between the proximal (upper) and distal (lower) portions of a wearer's leg. It has no structural arrangement for applying independently adjustable posteriorly and anteriorly directed forces against the tibia, nor does it have a structural arrangement capable of allowing independent vertical adjustment of the application points of such tibia directed forces.

SUMMARY OF THE INVENTION

Accordingly, it is an object of the present invention to provide a leg brace suitable for alleviating problems with one or both of a knee's cruciate ligaments.

A further object of the invention is to provide a leg brace that allows for the application against the tibia of separately adjustable amounts of anteriorly and posteriorly directed forces.

Yet a further object of the invention is to provide a leg brace that allows for independent vertical adjustment of the application points of anteriorly and posteriorly tibia directed forces.

Still another object of the present invention is to provide a leg brace allowing for independent vertical adjustment of tibia directed forces while providing adjustable hinge systems that allow the brace either to remain rigid or to bend in a fashion simulating the natural bending of the knee.

In accordance with a broad aspect of the present invention, there is provided a leg brace system for providing support to damaged or weakened anterior or posterior cruciate ligaments which includes an upper assembly extending generally longitudinally along the thigh, a lower assembly extending generally longitudinally along the calf, and hinge assemblies connecting the upper and lower assemblies and having their axes of rotation corresponding generally to the axis of rotation of the knee joint. Attached to the lower assembly and extending around the front of the leg just below the knee is an assembly for applying rearwardly directed force to the knee to prevent the tibia from sliding forward when the anterior cruciate ligament is damaged. A similar arrangement for directing force toward the front is mounted slightly lower on the lower leg and engages the rear of the leg at the upper portion of the calf to prevent the tibia from sliding to the rear when the posterior cruciate ligament is ruptured or damaged. The two assemblies for applying forward or rearwardly directed force to the tibia are independently adjustable, both as to tightness and vertical location.

In accordance with specific features of the present invention, a leg brace is provided which includes an upper assembly, a lower assembly and hinge assemblies connecting the upper and lower assemblies in the vicinity of the knee joint. The upper assembly is oriented generally longitudinally along the thigh and includes padding extending circumferentially around the thigh, a pair of elongate support struts extending respectively along the lateral and medial sides of the thigh, a pair of strut plates affixed to the padding and located generally near the upper ends of the support struts and having the upper ends of the support struts fastened to the strut plates, and straps extending circumferentially around the thigh and encompassing the padding and support struts.

In one embodiment of the invention, the padding material is circumferentially adjustable to accommodate wearers of varying thigh circumference. In the preferred embodiment, the padding is adjustable through use of a Velcro-type closure system.

Another aspect of one embodiment of the invention involves the use of adjustable elongate support struts to accommodate wearers of varying thigh length. In this embodiment, the upper ends of the support struts are provided with a series of small holes and the strut plates are provided with a series of correspondingly spaced holes. After the approximate desired strut length is selected, the closest set of strut holes and strut plate holes are aligned and the strut is affixed to the strut plate by inserting suitable fasteners, such as threaded bolts or other conventional fasteners in the aligned holes.

A further aspect of the invention is that the straps extending circumferentially around the thigh padding and support struts are adjustable so as to provide an appropriate amount of force for engaging the leg brace's upper assembly with the wearer's thigh.

Regarding another matter, the hinge assemblies connecting the leg brace's upper and lower assemblies may be of a single axis type, with their axes of rotation corresponding to the axis of rotation of the knee joint. Furthermore, the hinge assemblies may have an adjustable range of motion thereby allowing the brace to either remain rigid, to have a prescribed angular movement, or to bend in a fashion approximating the natural bending of the knee.

Concerning another aspect of the invention, the lower assembly is oriented generally longitudinally along the calf and includes padding extending circumferentially around the calf, a pair of elongate support struts extending respectively along the lateral and medial sides of the calf, a pair of strut plates affixed to the padding and located generally near the lower ends of the support struts and having the lower ends of the support struts fastened to the strut plates, straps extending circumferentially around the calf and encompassing the padding and support struts, and independent assemblies, affixed to the support struts, for applying variable amounts of posteriorly and anteriorly directed force against the upper portion of the tibia.

As discussed above in regard to the thigh padding, the calf padding may be circumferentially adjustable to accommodate calfs of various sizes. Furthermore, the lower assembly's elongate support struts may be adjustable in a fashion similar to that discussed above in connection with the upper assembly's support struts. In addition, the straps circumferentially encircling the lower assembly may be adjustable in a fashion similar to that discussed above with regard to the upper assembly's straps.

Concerning another aspect of the invention, the assembly for applying variable amounts of posteriorly directed force against the tibia is provided with an anterior cruciate ligament support plate and an adjustable anterior cruciate ligament support strap, the ends of which are affixed to the lower assembly's elongated support struts, preferably near the anterior edges thereof. Similarly, the assembly for applying variable amounts of anteriorly directed force against the tibia is provided with a posterior cruciate ligament support plate and an adjustable posterior cruciate ligament support strap the ends of which are affixed to the lower assembly's elongated support struts preferably near the posterior edges thereof. This aspect of the present invention allows for independent variation of the amount of anteriorly and posteriorly directed force that is directed against the tibia, thereby allowing the amount of cruciate ligament support provided by the leg brace to be varied according to the precise needs of each individual wearer.

Yet a further aspect of the present invention is that the assemblies for applying anteriorly and posteriorly directed force against the tibia may be independently vertically adjusted through the use of pairs of vertical slots in the elongate support struts to which the assemblies' support straps are affixed. In practice, the ends of the anterior cruciate ligament support strap may be slidably affixed to vertical slots running near the anterior edges of the lower assembly's elongate support struts and the ends of the posterior cruciate ligament support strap may be slidably affixed to vertical slots running near the posterior edges of the lower assembly's elongate support struts. In this fashion, the anterior and posterior cruciate ligament support plates may be independently vertically adjusted to accommodate the calf sizes of each individual wearer. It should be noted that regardless of how the cruciate ligament support plates are vertically adjusted, the anterior support plate will normally remain in a position superior to or higher than that of the posterior support plate, so that the anteriorly and posteriorly directed forces applied by the support plates may be properly oriented against the tibia. Accordingly, as an alternative, the two straps may be secured into a single slot in the lower leg struts.

Regarding yet a further aspect of one embodiment of the present invention, the bottom end of the lower assembly may be provided with an anti-pistoning support collar that includes an inner section of cushioning-type material, an outer section for adjusting the tightness of the collar about the lower leg and a pair of support struts extending respectively along the medial and lateral sides of the lower calf and having their upper ends affixed to the lower assembly's strut plates. By properly adjusting the collar around the portion of the lower leg immediately above the ankle, downward shifting of the leg brace from the pistoning effect of walking may be prevented. It should be noted that the cushioning material of the anti-pistoning collar may include conventional padding, or air-inflatable padding, in a circular configuration, or a pouch containing water-activated hardenable material, such as that disclosed in U.S. patent Application No. 198,152, filed May 24, 1988, that allows the collar's cushion to be custom formed around the wearer's leg at the time of application of the leg brace.

Other objects, features and advantages of the present invention will become apparent from a consideration of the following detailed description and from the accompanying drawings.

DETAILED DESCRIPTION OF PREFERRED EMBODIMENTS

Figure 1:
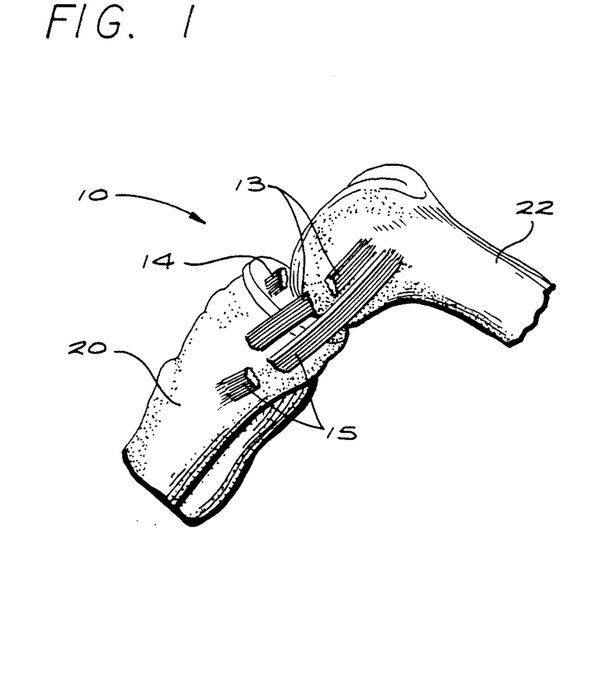
FIG. 1 is a pictorial representation of a knee joint with a damaged anterior cruciate ligament.
Figure 2:
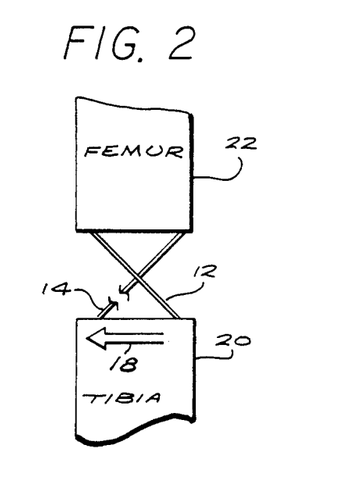
FIG. 2 is a diagrammatic representation of tibia instability resulting from a damaged anterior cruciate ligament.
Figure 3:
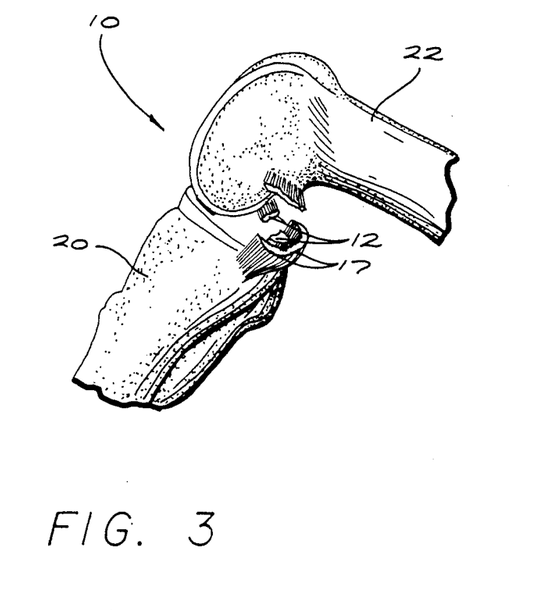
FIG. 3 is a pictorial representation of a knee joint with a damaged posterior cruciate ligament.
Figure 4:
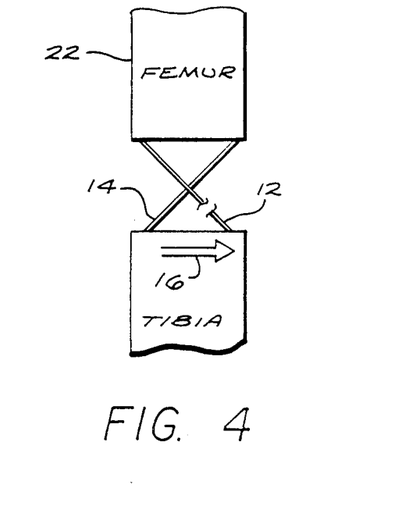
FIG. 4 is a diagrammatic representation of tibia instability resulting from a damaged posterior cruciate ligament.

Referring more particularly to the drawings, FIGS. 1, 2, 3 and 4 provide pictorial and diagrammatic representations of the knee joint 10, its posterior and anterior cruciate ligaments 12, 14, and the tibia instability resulting from torn or weakened posterior or anterior cruciate ligaments. Specifically, FIG. 1 pictures a knee joint 10 with a torn anterior cruciate ligament 14 and with the tibia 20 exhibiting excessive forward movement relative to the femur 22, and therefore having a positive anterior drawer sign. FIG. 2 provides a diagrammatic representation of a damaged anterior cruciate ligament 14 and the tibia instability associated with positive anterior drawer sign indicated by arrow 18. Similarly, FIG. 3 pictures a knew joint 10 with a damaged posterior cruciate ligament 12 and with the tibia 20 exhibiting excessive rearward movement relative to the femur 22 and therefore having a positive posterior drawer sign. FIG. 4 provides a diagrammatic representation of a damaged posterior cruciate ligament 12 and the tibia instability associated with positive posterior drawer sign indicated by arrow 16.

It is believed that the representation in FIGS. 1 through 4 will aid in understanding the functioning of the present invention. It is noted in passing that the medical diagram of FIG. 1 also shows a torn medial capsular ligament, and a torn tibial collateral ligament 15; and the medical diagram of FIG. 2 also shows torn posterior capsular, arcuate, and posterior oblique ligaments 17.

Figure 5:
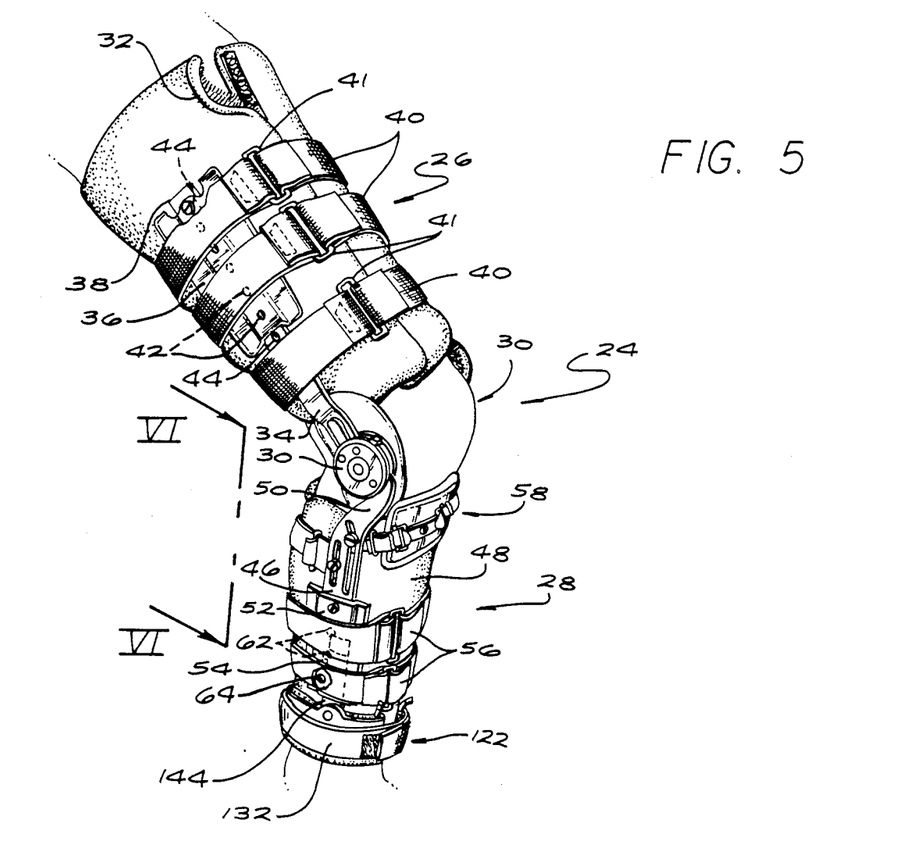
FIG. 5 is a perspective view of a cruciate ligament leg brace which illustrates the principles of the present invention.
Figure 6:
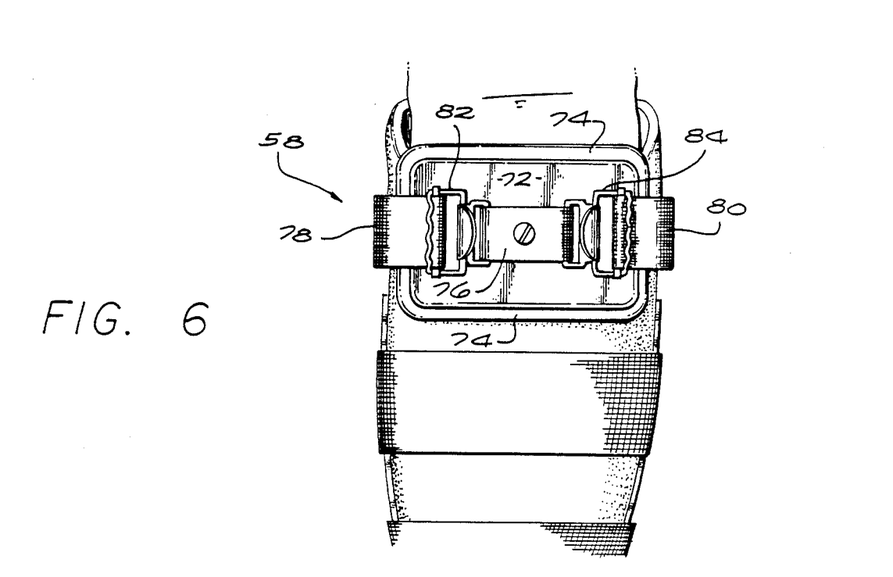
FIG. 6 is a view of a posterior cruciate ligament support plate taken along line VI—VI of FIG. 5.

Referring to FIG. 5, a perspective view of a leg brace 24 shows an upper assembly 26, a lower assembly 28 and hinge assemblies 30 joining the upper and lower assemblies 26 and 28.

The upper assembly 26 includes padding 32 extending circumferentially around the wearer's thigh, a pair of elongate support struts 34 extending respectively along the medial and lateral sides of the thigh, a pair of strut plates 36 affixed to the thigh padding 32 and positioned along the medial and lateral sides of the thigh so that the upper ends 38 of the upper assembly's support struts 34 may be affixed to the strut plates 36, and straps 40 affixed to, and extending circumferentially around, the thigh padding 32, support struts 34 and strut plates 36 for engaging the upper assembly 26 with the wearer's thigh. It may be noted that in the preferred embodiment the support struts 34 are made of a relatively lightweight but stiff material capable of resisting torsion and bending forces. High strength steel or engineering plastic strips may be used.

In accordance with one embodiment of the invention, as illustrated in FIG. 5, the upper assembly padding 32 is circumferentially adjustable to accommodate thighs of varying circumference. It may be noted that in the preferred embodiment the padding 32 is made adjustable through the use of a Velcro-type closure system, located at the overlapping edges of the padding.

As further illustrated in FIG. 5, the upper assembly's elongate support struts 34 may be adjusted in length to accommodate thighs of varying sizes. In accordance with this embodiment of the invention, the upper ends 38 of the support struts 34 include a series of small threaded holes 42, and the strut plates 36 include a series of correspondingly spaced holes 44. After the approximate desired strut length is selected, the strut holes 42 and strut plate holes 44 closest to one another are aligned and the struts 34 are fastened to the strut plates 36. Any conventional fastener, such as small, short bolts extending through holes 44 and threaded into tapped holes 42, may be used. It may be noted that the strut plates 36 may be fastened to the upper assembly padding 32 through the use of any conventional fastening arrangements including Velcro-type closures.

As also illustrated in FIG. 5, the straps 40 affixed to the upper assembly's padding 32 and extending circumferentially around the padding 32, support struts 34, and strut plates 36, are adjustable in order to allow for the application of an appropriate amount of force for engaging the leg brace's upper assembly 26 with the wearer's thigh. It should be noted that in the preferred embodiment the straps 40 are made of a strong yet flexible material like nylon and are made circumferentially adjustable through the use of a locking buckle or Velco fastening pads on the straps, which are used after the ends of the straps pass through the metal loops 41.

Figures 7, 8:
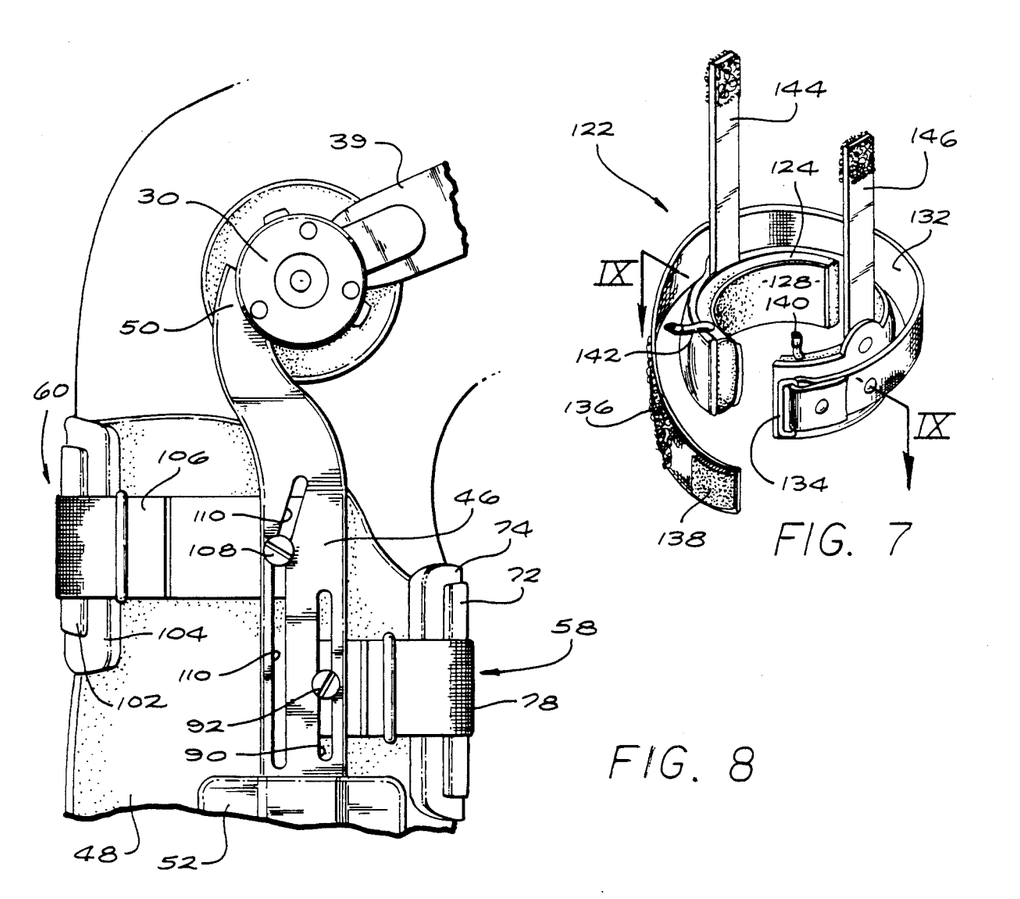
FIG. 7 is a perspective view of an anti-pistoning support collar while in an open position.
FIG. 8 is a side view of a cruciate ligament leg brace showing an adjustable hinge and independent vertical adjustment slots for anterior and posterior cruciate ligament support plates.

As is best illustrated in FIG. 8, the hinge assemblies 30 join together the leg brace's upper and lower assemblies 26 and 28. Joinder is achieved by having the lower ends 39 of the upper assembly's support struts 34 affixed to one side of the hinge assemblies 30 and by having the upper ends 50 of a second pair of elongate support struts 46, that are part of the lower assembly 28, affixed to the other side of the hinge assemblies 30. Additional purposes of the second pair of support struts 46 will be made clear in the description which follows. It may be noted that in accordance with one embodiment of the invention the hinge assemblies 30 are a single-axis type with their axes of rotation coinciding with the axis of rotation of the knee joint. It should also be noted that in the preferred embodiment the hinge assemblies 30 have an adjustable range of motion to allow the leg brace to either remain rigid, have limited motion, or to bend in a way approximately the natural bending of the knee.

As is best illustrated in FIGS. 5 and 8, the lower assembly 28 includes: padding 48 extending circumferentially around the wearer's calf; a second pair of elongate support struts 46 extending respectively along the medial and lateral sides of the calf and having their upper ends 50 affixed to one side of the hinge assemblies 30; a pair of strut plates 52 affixed to the calf padding 48 and positioned along the medial and lateral sides of the calf so that the lower ends 54 of the lower assembly's support struts 46 may be affixed to the strut plates 52; straps 56 affixed to and extending circumferentially around the calf padding 48, support struts 46 and strut plates 52 for engaging the lower assembly 28 with the wearer's calf; an assembly 58 for applying a variable amount of anteriorly directed force against the tibia 20; and an assembly 60 for applying a variable amount of posteriorly directed force against the tibia 20.

It should be noted that certain aspects of the present invention discussed above in connection with the leg brace's upper assembly 26 apply with equal force to the leg brace's lower assembly 28. Thus, in the preferred embodiment, the lower assembly's elongate support struts 46 are made of a relatively lightweight but stiff material capable of resisting torsion and bending forces. In addition, the lower assembly's straps 56 may be adjustable in a fashion similar to that described above in connection with the upper assembly's straps 40. Also, the lower assembly padding 48 is circumferentially adjustable to accommodate calfs of varying circumference, and in the preferred embodiment the padding 48 is made adjustable through use of a Velcro-type closure system. Further, the lower assembly's support struts 46 may have their lengths adjusted to accommodate calfs of varying sizes. Thus, in accordance with this embodiment of the invention, and the system described above in connection with the upper assembly's support struts 34, the lower ends 54 of the lower assembly's support struts 46 include a series of small holes 62 that may be aligned with correspondingly spaced holes 64 in the lower assembly's strut plates 52 after the approximate desired strut length is selected. The struts 46 are then affixed to the strut plates 52 by using conventional fasteners in the aligned holes 62 and 64.

The independently adjustable assemblies 58 and 60 constitute an important part of the invention. More specifically, the rear cruciate support assembly 58 includes the rear plate 72 having padding 74 secured to the inner surface thereof, and a metal bracket 76 to which the two straps 78 and 80 are secured by the metal loops 82 and 84 respectively. The strap 78, as shown in FIG. 8 is secured to the strut member 46 by a metal plate 88, which is in turn adjustably secured in slot 90 by threaded fastener 92. The straps 78 and 80 may be adjustably tightened by extending through one of the metal loops 82 and 84, and then being secured back upon the strap in question by mating Velcro surfaces.

The front cruciate support assembly 60 is similar in configuration to the rear plate described in detail hereinabove, and includes plate 102 and padding 104. Adjustable straps including strap 106 are adjustable in tightness as in the case of straps 78 and 80, and are vertically adjustable by screw 108, which may be selectively tightened at the desired vertical location in slot 110.

The front of the tibia, just below the knee has a bony protruberance or tubercle, and it is against this part of the tibia that the front plate 102 is preferably aligned. When an injury such as a torn anterior cruciate occurs, as indicated in FIGS. 1 and 2 of the drawings, the anterior cruciate ligament no longer prevents forward movement of the tibia relative to the femur, and the front assembly 60 is tightened up to the desired level to prevent any undesired subluxation. The rear assembly 58, however, may be maintained in a firm but somewhat looser state, as rearwardly directed subluxation or shifting of the tibia is not a problem with the posterior cruciate ligament intact.

On the other hand, in the case of the situation shown in FIGS. 3 and 4, where the posterior cruciate ligament is torn, the reverse arrangement is employed. Specifically, the rear assembly 58 is tightened, and the front assembly is held somewhat more loose, to encourage freedom of movement of the joint, as far as possible.

This independent adjustment of the assemblies for applying forwardly and rearwardly directed force to the upper portion of the tibia, both as to the force and as to the vertical location of the assemblies, is an important aspect of the invention.

Figure 9:
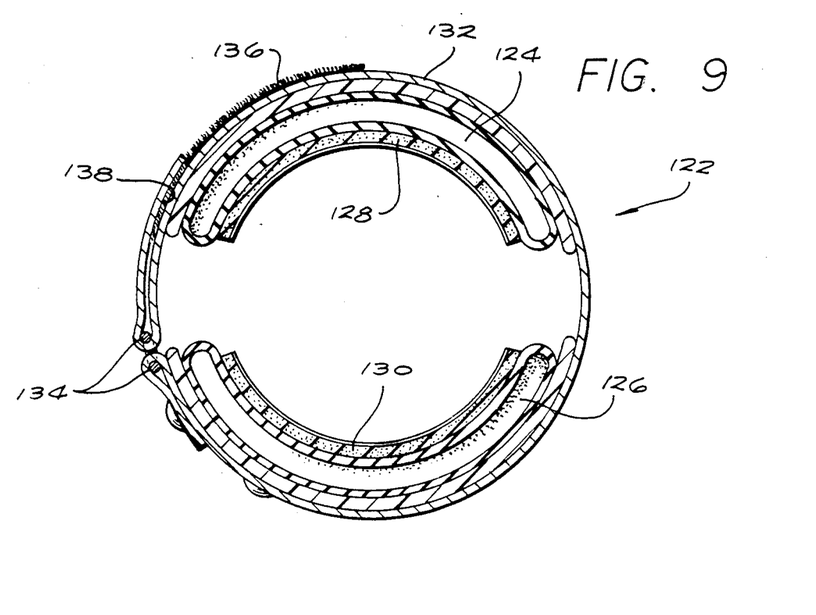
FIG. 9 is a cross-sectional view of an anti-pistoning support collar taken along line IX—IX of FIG. 7 and showing the collar in a closed position.

Referring now to FIGS. 5, 7 and 9 of the drawings, at the lower end of the prosthesis is an assembly 122 which serves to prevent "pistoning" of the appliance, which is the tendency, in the course of use of a substantial knee prosthesis of the present type, to shift downwardly on the leg.

More specifically, the subassembly 122 includes the inflatable bladders 124 and 126 which are intended to engage the ankle, either just above or just below the ankle bone protruberance. Within the two bladders 124 and 126, are the pads 128 and 130, which are intended to engage the ankle. Extending around the entire unit is the strap 132, which has at one end a metal loop 134 through which the strap 132 extends so that the strap may be folded back onto itself and so that mating Velcro pads 136 and 138 may engage one another and hold the anti-pistoning support firmly on the ankle.

The two semi-circular bladders 124 and 126 may be inflated in any suitable manner, for example, by the input tubes 140 and 142, which also include simple one-way valves to prevent loss of air.

The vertically extending support struts 144 and 146 are provided with Velcro pads at their other ends for engagement with the padding 48 and for enclosure within the straps 56, so that proper support of the remainder of the knee brace assembly 24 is accomplished.

In conclusion, it is to be understood that the foregoing description and accompanying drawings relate to one preferred illustrative embodiment of the present invention. Other embodiments may be utilized without departing from the spirit and scope of the invention. Thus, by way of example and not of limitation, the number of upper and lower assembly straps 40 and 56 respectively may be varied from one per assembly to four or more per assembly. Also, the hinge assemblies 30 could include polycentric rather than single axis hinges. Further, various parts of the invention could be made from materials other than those discussed herein. It is also noted that the anti-pistoning assembly could be used with other types of knee braces; and that in some cases a single strap, adjustable both vertically and as to tightness could be used for applying either anteriorly directed force or posteriorly directed force, and the other strap could be dispensed with, particularly if the prosthesis retention straps provide thorough support. Also, the vertical adjustment screw function could be accomplished by other mechanical arrangements, such as sliding vertical members and Velcro retention pads. Accordingly, it is to be understood that the detailed description and drawings set forth hereinabove are for illustrative purposes only and do not constitute a limitation on the scope of the invention.

What is claimed is:

1. A lightweight, easily removable leg brace for alleviating problems with torn or weakened anterior or posterior cruciate ligaments which comprises:
   an upper assembly oriented generally longitudinally along the thigh comprising:
   (a) padding extending circumferentially around the wearer's thigh;

(b) a first pair of elongate support struts extending along opposite sides of the thigh;

(c) means for affixing the upper ends of said first pair of support struts to said thigh padding; and (d) a plurality of adjustable straps extending circumferentially around said thigh padding and attached to said padding, a pair of hinge assemblies on opposite sides of the knee joint and respectively connected with the lower ends of said first pair of support struts;

a lower assembly oriented generally longitudinally along the tibia and the calf comprising:

(a) padding extending circumferentially around the wearer's calf;

(b) a second pair of elongate support struts extending along opposite sides of the calf and with their upper ends respectively connected to said hinge assemblies;

(c) means for affixing the lower ends of said second pair of support struts to said calf padding;

(d) a plurality of adjustable straps extending circumferentially around said calf padding and attached to said padding;

(e) posterior cruciate ligament support means for providing adjustable anteriorly directed force to the posterior of the calf, said posterior support means being affixed to said second pair of support struts;

(f) anterior cruciate ligament support means for providing adjustable posteriorly directed force to the anterior of the tibia adjacent the knee, said anterior support means being affixed to said second pair of support struts; and (g) means for independently vertically adjusting each of said posterior and anterior cruciate ligament support means, whereby said leg brace may be adjusted for use on legs of any size and for use with persons having injured anterior or posterior cruciate ligaments, or both.

2. A leg brace as defined in claim 1 wherein said means for affixing the upper ends of said first pair of support struts to said thigh padding and said means for affixing the lower ends of said second pair of support struts to said calf padding each include means for selectively varying the effective length of said first and second pairs of support struts thereby providing a leg brace suitable for use on all size legs.

3. A leg brace as defined in claim 1 wherein said lower assembly includes adjustable collar means at its lower end for circumferentially gripping the wearer's leg just above the ankle thereby preventing downward slippage of the leg brace during use.

4. A leg brace as defined in claim 1 wherein said hinge assemblies comprise single axis hinges having variable ranges of motion.

5. A leg brace as defined in claim 1 wherein each of said ligament support means extend substantially horizontally and constitute means for providing unidirectional force.

6. A lightweight, easily removable leg brace for alleviating problems with torn or weakened anterior or posterior cruciate ligaments which comprises:

an upper assembly oriented generally longitudinally along the thigh comprising:

(a) padding extending circumferentially around the wearer's thigh, said padding being adjustable to accommodate thighs of varying circumference;

(b) a pair of upper assembly strut plates affixed respectively to the lateral and medial sides of said thigh padding;

(c) a first pair of elongate support struts extending respectively along the lateral and medial sides of said thigh padding and having their upper ends affixed respectively to said upper assembly strut plates;

(d) a plurality of adjustable straps partially affixed to and extending circumferentially around said thigh padding and adapted to circumferentially grip the wearer's thigh;

a pair of hinge assemblies positioned on opposite sides of the knee joint with their axes of rotation roughly coinciding with the axis of rotation of the knee joint and being respectively connected with the lower ends of said first pair of support struts;

a lower assembly oriented generally longitudinally along the calf comprising:

(a) padding extending circumferentially around the wearer's calf, said padding being adjustable to accommodate calfs of varying circumference;

(b) a pair of lower assembly strut plates affixed respectively to the lateral and medial sides of said calf padding;

(c) a second pair of elongate support struts extending respectively along the lateral and medial sides of said calf padding and having their upper ends connected with said pair of hinge assembles and their lower ends affixed to said lower assembly strut plates;

(d) a plurality of adjustable straps partially affixed to and extending circumferentially around said calf padding and adapted to circumferentially grip the wearer's thigh;

(e) an adjustable anti-pistoning support collar affixed to the lower end of said lower assembly and adapted to circumferentially grip the wearer's leg just above the ankle thereby preventing downward slippage of the leg brace during use;

(f) a posterior cruciate ligament support assembly extending along the posterior of said calf padding and adapted to provide variable amounts of anteriorly directed force to the posterior of the calf, said posterior cruciate ligament support assembly being adjustably affixed to said second pair of elongate support struts;

(g) an anterior cruciate ligament support assembly extending along the anterior of said calf padding to provide variable amounts of posteriorly directed force to the anterior of the lower leg and adjacent the knee, said anterior cruciate ligament support assembly being adjustably affixed to said second pair of elongate support struts; and vertical positioning of each of said posterior and anterior support assemblies, whereby the area of application of said variable posteriorly and anteriorly directed forces may be varied to accommodate legs of any size.

7. a knee brace comprising:

an upper pair of struts;

a lower pair of struts;

means for mounting said upper pair of struts on the inner and outer sides of the thigh;

means for mounting said lower pair of struts on the inner and outer sides of the lower leg;

means for pivotally connecting said upper and lower pairs of struts to simulate functional knee movement;

means for applying adjustable rearwardly directed force to the front of the tibia immediately adjacent the knee to restrict forward subluxation of the tibia relative to the femur;

means for mounting said rearwardly directed force applying means on, and vertically adjusting the position of said force applying means with respect to said lower pair of struts;

means for applying adjustable forwardly directed force to the rear of the lower leg near the upper portion of the calf to restrict rearward subluxation of the tibia relative to the femur;

means for mounting and vertically adjusting said means for applying forwardly directed force with respect to said lower pair of struts; and said means for applying rearwardly directed force being independent from said means for applying forwardly directed force to the tibia.

8. A knee brace as defined in claim 7 further comprising anti-pistoning means for preventing downward displacement of said knee brace, including means for resiliently engaging the ankle of a user and mechanically supporting said brace.

9. A knee brace as defined in claim 8 wherein said means for resiliently engaging the ankle includes at least one inflatable bladder.

10. A knee brace as defined in claim 8 wherein said means for resiliently engaging the ankle includes inflatable means for encompassing the ankle.

11. A knee brace as defined in claim 9 including adjustable strap means for holding said inflatable bladder against the ankle.

12. A knee brace as defined in claim 7 wherein said force applying means includes a padded plate and adjustable strap means for securing said plate to said lower pair of struts.

13. A knee brace as defined in claim 8 further comprising padded means for engaging the upper and lower leg and means for securing said struts to said padded means.

14. A knee brace comprising:
an upper pair of struts;
a lower pair of struts;
means for mounting said upper pair of struts on the inner and outer sides of the thigh;
means for mounting said lower pair of struts on the inner and outer sides of the lower leg;
means for pivotally connecting said upper and lower pairs of struts to simulate limited normal knee movement;
means for applying force to the tibia adjacent the knee to restrict subluxation of the tibia relative to the femur; and
anti-pistoning means for preventing downward displacement of said knee brace, including means for resiliently engaging the ankle of a user immediately above the ankle bone protruberance, and mechanically supporting said brace.

15. A knee brace as defined in claim 14 wherein said means for resiliently engaging the ankle includes at least one inflatable bladder.

16. A knee brace as defined in claim 14 wherein said means for resiliently engaging the ankle includes inflatable means for encompassing the ankle.

17. A knee brace as defined in claim 15 including adjustable strap means for holding said inflatable bladder against the ankle.

18. a knee brace comprising:
an upper pair of struts;
a lower pair of struts;
means for mounting said upper pair of struts on the inner and outer sides of the thigh;
means for mounting said lower pair of struts on the inner and outer sides of the lower leg;
means for pivotally connecting said upper and lower pairs of struts to simulate functional knee movement;
means for applying adjustable unidirectional force to the tibia adjacent the knee to restrict subluxation of the tibia relative the femur;
means for mounting said force applying means on said lower pair of struts;
means for vertically adjusting said force applying means;
means for applying said adjustable unidirectional force substantially only to the front of said tibia; and
means for applying said adjustable unidirectional force substantially only to the upper part of the calf at the rear of the lower leg.

19. A knee brace as defined in claim 18 further comprising anti-pistoning means for preventing downward displacement of said knee brace, including means for resiliently engaging the ankle of a user and mechanically supporting said brace.

20. A leg brace as defined in claim 1 wherein each of said ligament support means is positioned in the proximal third of the tibia.

21. A leg brace as defined in claim 7 wherein each of said force applying means is positioned in the proximal third of the tibia.

22. A leg brace as defined in claim 18 wherein said means for applying adjustable unidirectional force to the tibia is positioned in the proximal half of the tibia.

23. A leg brace as defined in claim 7 wherein:
said means for mounting said rearwardly directed force applying means includes an adjustable strap assembly extending generally from said inner lower strut to said outer lower strut and only across the anterior portion of the calf; and
said means for mounting said forwardly directed force applying means includes an adjustable strap assembly extending generally from said inner lower strut to said outer lower strut and only across the posterior portion of the calf.

24. A leg brace as claimed in claim 1 wherein:
said posterior cruciate ligament support means is affixed to said second pair of elongate support struts by an adjustable strap assembly extending generally between said second pair of elongate support struts and across the posterior portion of the upper calf; and
said interior cruciate ligament support means is affixed to said second pair of elongate support struts by an adjustable strap assembly extending generally between said second pair of elongate support struts and across the anterior portion of the upper calf.

25. A leg brace as claimed in claim 8 wherein:
said means for mounting said rearwardly directed force applying means includes an adjustable strap assembly extending generally from said inner lower strut to said outer lower strut and across the anterior portion of the calf; and said means for mounting said forwardly directed force applying means includes an adjustable strap assembly extending generally from said inner lower strut to said outer lower strut and across the posterior portion of the calf.

26. A leg brace as claimed in claim 25 further comprising padded means for circumferentially engaging the upper and lower leg and means for securing said upper and lower struts to said padded means.

27. A knee brace comprising:

an upper pair of struts;

a lower pair of struts;

means for mounting said upper pair of struts on the inner and outer sides of the thigh;

means for mounting said lower pair of struts on the inner and outer sides of the lower leg;

means for pivotally connecting said upper and lower pairs of struts to simulate limited normal knee movement;

means for applying adjustable rearwardly directed force to the front of the tibia immediately adjacent the knee to restrict forward subluxation of the tibia relative to the femur;

means for mounting said rearwardly directed force applying means on said lower pair of struts, said rearwardly directed force applying means extending only around the front of the tibia between said inner and outer lower struts;

means for applying adjustable forwardly directed force to the rear of the lower leg at the upper portion of the calf to restrict rearward subluxation of the tibia relative to the femur; and means for mounting said means for applying forwardly directed force on said lower pair of struts, said means for applying forwardly directed force extending only around the rear of the calf between said inner and outer lower struts.

* * * * *